# (12) United States Patent
Bray, III

(10) Patent No.: US 7,674,817 B2
(45) Date of Patent: Mar. 9, 2010

(54) ANTIMICROBIAL ACID-CATALYZED COATING COMPOSITIONS

(75) Inventor: James H. Bray, III, Roanoke, VA (US)

(73) Assignee: Akzo Nobel Coatings International B.V., Arnhem (NL)

(\*) Notice: Subject to any disclaimer, the term of this patent is extended or adjusted under 35 U.S.C. 154(b) by 0 days.

(21) Appl. No.: 11/127,394

(22) Filed: May 12, 2005

(65) Prior Publication Data

US 2005/0256292 A1    Nov. 17, 2005

Related U.S. Application Data

(60) Provisional application No. 60/570,214, filed on May 12, 2004.

(51) Int. Cl.
C08G 63/02   (2006.01)
C09D 5/14    (2006.01)

(52) U.S. Cl. .................. 514/416; 514/417; 514/717; 514/718; 514/724; 514/734; 514/706; 514/735; 523/122; 106/15.05

(58) Field of Classification Search .......... 523/122; 106/15.05
See application file for complete search history.

(56) References Cited

U.S. PATENT DOCUMENTS

| | | | | |
|---|---|---|---|---|
| 4,740,398 | A * | 4/1988 | Bouchette | 428/28 |
| 5,135,964 | A | 8/1992 | Lee et al. | 522/96 |
| 5,182,379 | A * | 1/1993 | Cook et al. | 536/63 |
| 5,360,843 | A * | 11/1994 | Edgar et al. | 524/41 |
| 5,698,229 | A * | 12/1997 | Ohsumi et al. | 424/604 |
| 6,102,205 | A * | 8/2000 | Greff et al. | 206/438 |
| 6,231,875 | B1 * | 5/2001 | Sun et al. | 424/401 |
| 7,098,256 | B2 | 8/2006 | Ong et al. | 522/97 |
| 2002/0106413 | A1 * | 8/2002 | Herbst et al. | 424/600 |

FOREIGN PATENT DOCUMENTS

| | | | |
|---|---|---|---|
| JP | 2004-154779 | * | 3/2004 |
| JP | 2004-154779 A | | 3/2004 |
| WO | WO 97/46627 A1 | | 12/1997 |
| WO | WO 03/054045 | * | 7/2003 |
| WO | WO 2004/085451 A2 | | 10/2004 |
| WO | WO 2004/085451 A3 | | 10/2004 |

OTHER PUBLICATIONS

Derwent abstract 2005-146093/16 abstracting JP 2005 028209-A.
Derwent abstract 2005-142275/15 abstracting WO 2005007758-A2 (3 pages).
Derwent abstract 2005-134009/15 abstracting EP 1502508-A2 (2 pages).
Derwent abstract 2005-142280/15 abstracting WO 2005007817-A2 (2 pages).
""Covalon Technologies Inc receives USA Patent And European Patent Certificate for anti-microbial coating technology applied to implantable medical devices,"" Press Release, Apr. 20, 2005 (1 page).
""Antimicrobial radiation curable coating,"" abstract of Publication No. 20050080158/US-A1.
""Antimicrobial adhesive and coating substance and method for the production thereof,"" abstract of Publication No. 20050080157/US-A1.
""Derivatives of andrimide and moiramide b having antibacterial properties,"" abstract of Publication No. 20050080129/US-A1.
""Process for the antimicrobial treatment of fiber materials,"" abstract of Publication No. 20050080044/US-A1.
""Self-preserved antibacterial nasal, inhalable, and topical ophthalmic preparations and medications,"" abstract of Publication No. 20050080043/US-A1.
""Two-sided antimicrobial wipe or pad,"" abstract of Publication No. 20050079987/US-A1.
""Antimicrobial composition,"" abstract of Publication No. 20050079597/US-A1.
""Biocidal polymers,"" abstract of Publication No. 20050079150/US-A1.
Fabric article treating device and system with anti-microbial agent, abstract of Publication No. 20050076532/US-A1.
""Miller Paint introduces First NW Paint Product to Inhibit Microbe Growth,"" Internet pcimag article, Jul. 1, 2003 (6 pages).
Sanitized® Brand Bacteriostat PDQ Powder, Product Information Sheet.
American Chemical Society, CAS Registry No. 3380-34-5, 1998 (2 pages).
""Antimicrobials for household products,"" Ciba Product Information, Jun. 24, 1999 (2 pages).
Johns, K. ""Hygienic coatings: The next generation,"" Surface Coatings International Part B: Coatings Transactions, vol. 86, B2, 91-168, pp. 101-110 (Jun. 2003).
International Search Report No. PCT/EP2005/052095 dated Oct. 18, 2005.
Written Opinion of PCT/EP2005/05209 dated Oct. 18, 2005.
Patent Abstracts of Japan abstracting JP 2004-154779 A.
International Preliminary Report for application No. PCT/EP2005/052095 dated Jul. 19, 2006.
Dieter Stoye et al, ""Resins for Coatings: chemistry, properties, and applications,"" pp. 102-103 & 116 (1996).

\* cited by examiner

*Primary Examiner*—Irina S Zemel
(74) *Attorney, Agent, or Firm*—Laine K. Parker; Louis A. Morris; Ralph J. Mancini

(57) ABSTRACT

The antimicrobial acid-catalyzed coating composition of the invention is an acid-catalyzed coating composition formulated with at least one antimicrobial agent to provide antimicrobial activity to the coating composition and an article coated therewith.

3 Claims, 2 Drawing Sheets"

Staphylococcus aureus ATCC 9144
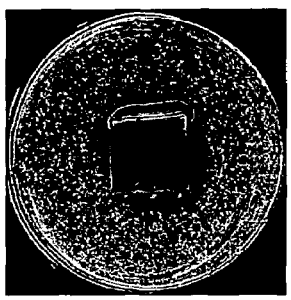
Fig. 1 Comp. Ex. 4
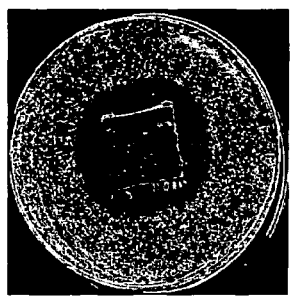
Fig. 2 Ex. 5
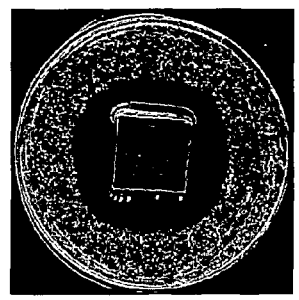
Fig. 3 Ex. 6
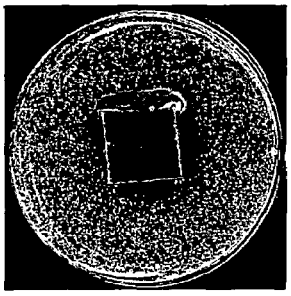
Fig. 4 Comp. Ex. 9
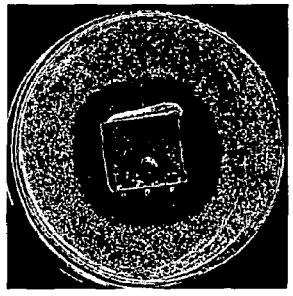
Fig. 5 Ex. 10
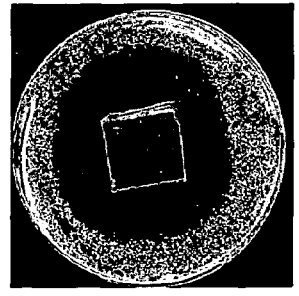
Fig. 6 Ex. 11

Escherichia coli NCTC 8196
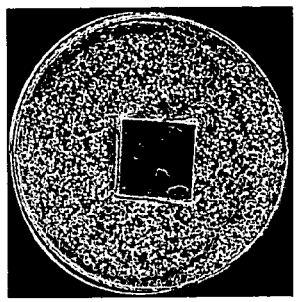
Fig. 7 Comp. Ex. 4
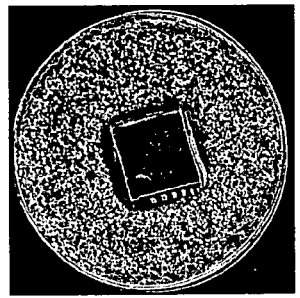
Fig. 8 Ex. 5
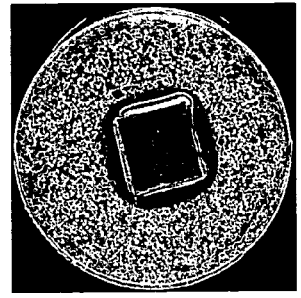
Fig. 9 Ex. 6
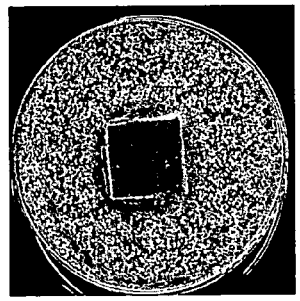
Fig. 10 Comp. Ex. 9
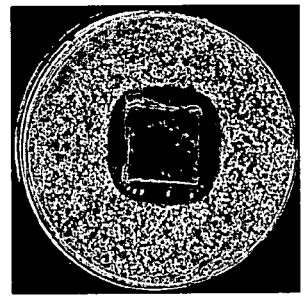
Fig. 11 Ex. 10
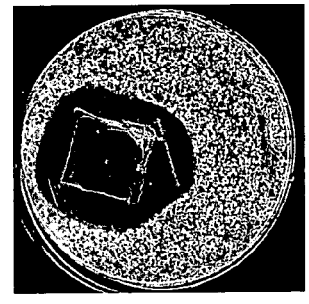
Fig. 12 Ex. 11

ANTIMICROBIAL ACID-CATALYZED COATING COMPOSITIONS

This application claims priority from U.S. Provisional Patent Application No. 60/570,214, filed May 12, 2004.

BACKGROUND OF THE INVENTION

The present invention relates to acid-catalyzed coating compositions having an antimicrobial agent(s) ("antimicrobial acid-catalyzed coating compositions"), coatings formed from antimicrobial acid-catalyzed coating compositions, and articles of manufacture having such coatings.

Acid-catalyzed coatings are known for their superior physical properties, such as moisture and stain resistance, adhesion and wear resistance. These properties are due to the crosslinking of the polymers by an acid catalyst.

Generally, acid-catalyzed coating compositions are simply polymers crosslinked as a result of a reaction catalyzed by an acid. They usually have four components:
1. a crosslinking resin or resins, in many cases an aminoplast (e.g., urea-formaldehyde, melamine-formaldehyde, etc.);
2. one or more backbone resins (e.g., alkyds, acrylics, polyurethanes, etc.), which contain functional groups that will react with the crosslinking resin(s);
3. one or more carriers (water and/or organic solvents, blends of organic sovents with or without water) for transporting the resins to the article to be finished; and
4. one or more acid catalysts (e.g., para-toluene sulfonic acid (p-TSA), toluene sulfonic acid (TSA), phenyl acid phosphate, n-butyl acid phosphate, etc.).

SUMMARY OF THE INVENTION

It has been found that acid-catalyzed coating compositions having antimicrobial properties can be formulated. These coating compositions provide finished coatings having antimicrobial properties while maintaining other desired coatings properties.

In accordance with the invention, an antimicrobial agent is added to an acid-catalyzed coating composition to provide a coating with antimicrobial properties.

BRIEF DESCRIPTION OF THE DRAWINGS

FIGS. 1-12 show the results of bacterial growth inhibition testing as described in the examples.

DETAILED DESCRIPTION OF THE INVENTION

An antimicrobial acid-catalyzed coating composition can be formulated by adding an antimicrobial agent to an acid-catalyzed coating composition. The formulation and manufacture of acid-catalyzed coatings are known generally in the art and are commercially available under product names such as REL-VIRON, REL-PRIME, REL-PLAZ, AQUA-PLAZ and REL-VETTE, all available from Akzo Nobel Coatings Inc., High Point, N.C. Acid-catalyzed coating compositions can be solvent-borne or water-borne.

As discussed herein, acid-catalyzed coating compositions generally have four components; one or more crosslinking resins, one or more backbone resins, one or more carriers, and one or more acid catalysts. The present invention adds an antimicrobial agent to the formulation for an acid-catalyzed coating composition. These elements are described in more detail below.

The crosslinking resin or resins is usually an aminoplast. Representative examples of the crosslinker include, but are not limited to, one or more of the following resins: melamine formaldehyde, blend of urea and melamine formaldehyde, urea formaldehyde, etc. The selection of the crosslinker can influence the coating's cure speed, chemical and water resistance, and formaldehyde emission.

The backbone resin(s) operates to plasticize the crosslinker and provide the applied film with toughness and flexibility. In addition, the backbone resin(s) also influences other film properties and is selected based on the desired properties. Some of these properties include: cure speed, sandability, surface hardness, water resistance, color or light fastness, and inherent film color (colorless or water white versus slightly amber).

Representative examples of the backbone resin include, but are not limited to the following resins, or combinations thereof: alkyds, acrylics, acrylic polyols (e.g., styrene acrylics, etc.), polyurethanes, cellulose esters/modified cellulose products, vinyl resins, nitrocellulose resins, etc. These resins have functional groups for reacting with the crosslinker. For example, the resins can be modified by any number/type of polymers (e.g., nitrocellulose, vinyl, cellulose acetate butyrate (CAB), etc.) to yield the desired functional group(s).

Two common alkyds are coconut oil alkyds and tall oil fatty acid (TOFA) alkyds. Also, alkyds can be obtained from soya oil, linseed oil, corn oil, castor oil, etc. and are usually chosen based on oil length.

Representative examples of modified cellulose products/cellulose esters include, among others, nitrocellulose, cellulose acetate butyrate (CAB), etc.

A variety of vinyls are used in acid-catalyzed coating compositions. They are generally selected for enhancing adhesion, flexibility and chemical resistance.

Although these backbone resins are most common to solvent borne acid-catalyzed coating compositions, most of them also exist in either a dispersed, colloidal or water-reducible form (e.g., an emulsion), and can therefore be used in water-borne systems as well.

The acid-catalyzed coating composition can include one or more crosslinker in any combination with one or more backbone resins. Representative, non-limiting examples of which include:

Acrylic backbone resin and urea formaldehyde crosslinker;
Coconut alkyd and cellulose ester backbone resins, and a blend of urea and melamine formaldehyde crosslinker;
A blend of alkyd, acrylic polyol, and nitrocellulose as the backbone resin, and a urea formaldehyde resin crosslinker;
A blend of alkyd and vinyl resins as the backbone resins, with a melamine formaldehyde crosslinker;
Styrene acrylic emulsion backbone resin and a urea formaldehyde resin crosslinker;
A coconut alkyd, or castor oil combined with an acrylic polyol as the backbone resins, with a melamine formaldehyde crosslinker;
Short oil coconut or tall oil fatty acid alkyd backbone resin, and a blend of urea and melamine formaldehyde crosslinker;
Tall oil fatty acid alkyd backbone resin, and a blend of urea and melamine formaldehyde crosslinker; etc.

In any coating, the role of the carrier is to deliver the coating to the substrate. The carrier also performs some more specific roles in both solvent-borne and water-borne coatings. For solvent-borne coatings, this involves solubilizing the binders and aiding in the flow and leveling of the delivered coating. Typical solvent-borne carriers include a variety of organic solvents such as alcohols, aliphatic and aromatic hydrocarbons, esters, ketones, etc. In water-borne coatings, the main carrier is water. Other carriers common to water-borne coatings are coalescing solvents, which help join the discrete acrylic particles into a uniform film, and alcohols.

The type and amount of catalyst can be selected depending on whether the coating is pre-catalyzed (one pack) or post-catalyzed (two pack). Representative examples of the catalyst include, but are not limited to, para-toluene sulfonic acid (p-TSA), phenyl acid phosphate (PAP), butyl acid phosphate (BAP), etc. Of these, p-TSA is generally used for post-catalyzed coatings, in an amount of 1-10%, 2-8%, by weight acid non-volatile, while the others are usually used for pre-catalyzed coatings, in an amount of 1-10%, 2-5%, by weight acid non-volatile.

A variety of antimicrobial agents are available in both organic and inorganic forms. Either type or mixtures of organic and inorganic antimicrobial agent(s) can be used in the acid-catalyzed coating composition of the invention. Triclosan (2,4,4-trichloro-2-hydroxydiphenyl ether), sold by Ciba under the name Irgaguard B1000, and Clariant's PDQ (N-(trichloromethylthio)phthalimide) are both organic antimicrobial agents. Inorganic antimicrobials are usually silver-based, such as AlphaSan from Milliken Chemical and Irgaguard B5000 from Ciba. The antimicrobial agent functions to inhibit bacterial, fungal, microbial and other pathogen or non-pathogen growth by controlling the growth of microorganisms on contact with a surface coated by the composition of the present invention.

Other additives normally used in coatings, especially acid-catalyzed coatings, and those used in antimicrobial compositions, can be included as well. Representative examples of such additives include, but are not limited to, wetting agents, defoaming agents, anti-sag agents, pigments, sheen controllers, plasticizers, (e.g., DINP (di-isonomylphthalate), etc.), stabilizers, alcohols (e.g., butanol, isobutanol, ethanol, etc.), silicone flow agents, other flow agents, polysiloxanes, polyethers, silica, polyethylene wax, polypropylene wax, etc.

Acid-catalyzed coatings may be applied by any method known in the art, including without limitation spraying, brushing, rolling, dipping, etc. They can be air dried and/or oven dried. For oven drying, dwell times are often dependent on the configuration and operation of the finishing line. It is desirable to have longer dwell times (the length of time at the recommended Board/substrate Surface Temperature (BST)) at higher BSTs. Usual cure conditions for an acid catalyzed coating are about 120° F.—about 150° F. BST, about 130° F.—about 140° F. BST, for about 1—about 20 minutes, about 5—about 15 minutes. The average is about 130° F. (about 54° C.) BST for about 5 minutes. The maximum safe BST is dependent on the substrate.

Substrates to be coated with antimicrobial acid-catalyzed coatings also vary widely including without limitation, wood, plastic, metal, etc. It is desirable for many surfaces to have antimicrobial properties, various furnishings, cabinets, counters, floors, etc. Some non-limiting examples of areas for such coatings are in the home, especially the kitchen and bathroom, the office, especially medical offices (desks, etc.), hospitals, etc., anywhere that is susceptible to bacterial/microbial contamination.

Typical ranges of components in the antimicrobial acid-catalyzed coating composition are listed below:
Backbone resin: about 40—about 60% by weight of non-volatiles
Crosslinker: about 20—about 40% by weight of non-volatiles
Carrier: about 60—about 70% by weight of volatiles
Catalyst: about 2—about 4% by weight of non-volatiles
Antimicrobial agent: about 0.1—about 1% by weight of non-volatiles.

The range of volatiles by weight in an acid-catalyzed coating is usually about 40 to about 95%.

Components and typical ranges of components in an acid-catalyzed coating are listed below in % by weight of non-volatiles:

| | |
|---|---|
| Oils and Alkyd Resins | about 5 to about 60%, about 10-about 50%, about 20-about 40% |
| Urea-formaldehyde Resins | about 5 to about 60%, about 10-about 50%, about 20-about 40% |
| Melamine-formaldehyde Resins | about 5 to about 60%, about 10-about 50%, about 20-about 40% |
| Nitrocellulose Resin | about 1 to about 40%, about 10-about 30%, about 5-about 20% |
| Vinyl Resin | about 1 to about 40%, about 10-about 30%, about 5-about 20% |
| Cellulose Acetate Butyrate | about 1 to about 40%, about 10-about 30%, about 5-about 20% |
| Para-Toluene Sulfonic Acid | about 1 to about 10%, about 2-about 8%, about 3-about 5% |
| Toluene Sulfonic Acid | about 1 to about 10%, about 2-about 8%, about 3-about 5% |
| Phenyl Acid Phosphate | about 1 to about 10%, about 2-about 8%, about 3-about 5% |
| n-Butyl Acid Phosphate | about 1 to about 10%, about 2-about 8%, about 3-about 5% |

A list of solvents and typical ranges for their use in an acid-catalyzed coating are identified in % by weight of volatiles:

| | |
|---|---|
| Methyl Alcohol | about 1 to about 60%, about 5-about 50%, about 10-about 20% |
| Ethyl Alcohol | about 1 to about 60%, about 5-about 50%, about 10-about 20% |
| Isopropyl | about 1 to about 60%, about 5-about 50%, about 10-about 20% |
| n-Propyl Alcohol | about 1 to about 60%, about 5-about 50%, about 10-about 20% |
| Isobutyl Alcohol | about 1 to about 60%, about 5-about 50%, about 10-about 20% |
| n-Butyl Alcohol | about 1 to about 60%, about 5-about 50%, about 10-about 20% |
| Amyl Alcohol | about 1 to about 60%, about 5-about 50%, about 10-about 20% |
| Toluene | about 1 to about 90%, about 10-about 80%, about 20-about 60% |
| Xylene | about 1 to about 90%, about 10-about 80%, about 20-about 60% |
| 1,2,4-Trimethylbenzene | about 1 to about 90%, about 10-about 80%, about 20-about 60% |
| Acetone | about 1 to about 90%, about 10-about 80%, about 20-about 60% |
| n-Butyl Acetate | about 1 to about 90%, about 10-about 80%, about 20-about 60% |
| Isobutyl Acetate | about 1 to about 90%, about 10-about 80%, about 20-about 60% |
| n-Pentyl Proprionate | about 1 to about 90%, about 10-about 80%, about 20-about 60%. |

The range of volatiles by weight in an acid-catalyzed coating is about 40 to about 95%.

Typical ranges for the antimicrobial agent are identified in percentages by weight of non-volatiles: about 0.01—about 10%, about 0.25—about 0.5%, about 1—about 5%, about 3—about 8%.

EXAMPLES

Formulation Example 1

|  | % Weight |
|---|---|
| Xylene | 31.400 |
| Alkyd | 21.100 |
| Isobutyl Alcohol | 19.200 |
| Naphtha | 12.244 |
| Urea-Formaldehyde Resin | 8.800 |
| Melamine-Formaldehyde Resin | 5.263 |
| Para Toluene Sulfonic Acid | 1.900 |
| Antimicrobial Agent | 0.093 |

The antimicrobial agent has been calculated as 0.25% by weight of non-volatiles.

Formulation Example 2

|  | % Weight |
|---|---|
| Alkyd and acrylic polyol backbone | 14.220 |
| Urea-Formaldehyde Resin | 4.650 |
| Carrier | 72.392 |
| Nitrocellulose | 5.700 |
| Phthalate plasticizer | 2.850 |
| Catalyst | 0.120 |
| Antimicrobial Agent | 0.068 |

The antimicrobial agent has been calculated as 0.25% by weight of non-volatiles.

Formulation Example 3

|  | % Weight |
|---|---|
| Alkyd and acrylic polyol backbone | 26.800 |
| Melamine formaldehyde resin | 6.700 |
| Carrier | 63.535 |
| Nitrocellulose | 0.880 |
| Catalyst | 2.000 |
| Antimicrobial Agent | 0.085 |

The antimicrobial agent has been calculated as 0.25% by weight of non-volatiles.

Examples 1-2 and Comparative Example 3

For Examples 1 and 2, two REL-VIRON topcoat formulations (available from Akzo Nobel Coatings Inc.) were modified by the addition of Irgaguard B 1000 (available from Ciba Specialty Chemicals), an antimicrobial agent. The Irgaguard B 1000 was mixed into the first REL-VIRON topcoat to a concentration of 0.25% by weight of non-volatiles and into the second to a concentration of 0.5% by weight of non-volatiles. Two test panels of maple, cherry and walnut, which had been stained and sealed, were sprayed with the antimicrobial REL-VIRON topcoats to a thickness of about 3 wet mils. The coated panels were flash dried at ambient temperature for 15 minutes, then oven dried for 15 minutes at 135 degrees F., then cooled to ambient temperature. The finished panels were allowed to age for approximately 2 weeks. The coated panels were tested for typical coating properties. These tests and the results are reported in Table 1 below.

For antimicrobial tests, the panels were placed in an approximately 2×2 cm diameter sample of agar (casin-soy meal peptone) containing bacteria from a diluted overnight culture (0.85% NaCl solution pH 7.2+/−0.2 for dilution) of *Staphylocuccus areus* ATTCC 9144 and a similar sample containing *Escherichia coli* NCTC 8196. The antimicrobial activity was evaluated by both zone of inhibition and the Vinson Rating after incubation at 37 degrees C. for 24 hours. Both evaluation methods indicated good antimicrobial activity.

Comparative Example 3

A comparative test panel was prepared in the same manner as described in the above Examples 1-2, except no antimicrobial agent was added to the REL-VIRON topcoat. The coated panel was tested for typical coating properties. These tests and the results are reported in Table 1 below.

The comparative test panel was also tested for antimicrobial activity according to the method described in the Examples. No antimicrobial activity was indicated.

TABLE 1

|  | ASTM | Ex. 1 0.25% | Ex. 2 0.50% | Comp. Ex. 3 0% |
|---|---|---|---|---|
| PLASTICIZER MIGRATION |  |  |  |  |
| HOT | D-2199 | No Change | No Change | No Change |
| COLD | D-2199 | No Change | No Change | No Change |
| COLD CHECK TEST 10 CY | D 1211 | PASS | PASS | PASS |
| DFT | D 6132 (ON WOOD) | 2.4 MILS | 2.3 MILS | 2.2 MILS |
| STAIN RESISTANCE TEST |  |  |  |  |
| 10% CITRIC ACID | D 1308, 3.1.1 | 10 | 10 | 10 |
| WATER | D 1308, 3.1.1 | 10 | 10 | 10 |

TABLE 1-continued

|  | ASTM | Ex. 1 0.25% | Ex. 2 0.50% | Comp. Ex. 3 0% |
|---|---|---|---|---|
| MUSTARD | D 1308, 3.1.1 | 10 | 10 | 10 |
| IODINE | D 1308, 3.1.1 | 10 | 10 | 10 |
| INK | D 1308, 3.1.1 | 10 | 10 | 10 |
| COFFEE | D 1308, 3.1.1 | 10 | 10 | 10 |
| AMMONIA | D 1308, 3.1.1 | 10 | 10 | 8 |
| RUBBING ALCOHOL | D 1308, 3.1.1 | 10 | 10 | 6 |
| VINEGAR | D 1308, 3.1.1 | 10 | 10 | 10 |
| NAPTHA | D 1308, 3.1.1 | 10 | 10 | 10 |
| ACETONE | D 1308, 3.1.1 | 10 | 10 | 10 |
| LIQUID JOY | D 1308, 3.1.1 | 10 | 10 | 10 |
| FINGERNAIL POLISH | D 1308, 3.1.1 | 10 | 10 | 10 |
| MERTHIOLATE | D 1308, 3.1.1 | 10 | 10 | 10 |
| FADE RESISTANCE | G-53 | 8 | 8 | 8 |
| ADHESION (MAR BAR)* | D-5178 (MODIFIED) | PASS | PASS | PASS |

*Modification is the use of the Model 1001 Organic Coatings adhesion tester in place of the Belmar (Balanced Beam) tester.
Ratings:
1 = Fail,
10 = No effect Comparative Example 4 and Examples 5-8

In Comparative Example 4, a test panel was sprayed with REL-VIRON (available from Akzo Nobel Coatings Inc.). In Examples 5-8, the percentages of antimicrobial agent are given by weight of non-volatiles. Example 5 is a test panel sprayed with REL-VIRON formulated with 0.25% Ciba's IRGAGUARD B1000. Example 6 is a test panel sprayed with REL-VIRON formulated with 0.5% Ciba's IRGAGUARD B1000. Example 7 is a test panel sprayed with REL-VIRON formulated with 0.25% Clariant's PDQ. Example 8 is a test panel sprayed with REL-VIRON formulated with 0.5% Clariant's PDQ.

The coating properties of Comparative Example 4 and Examples 5-8 were tested and the results are shown in Table 2.

TABLE 2

|  | ASTM Reference | Comp. Ex. 4 | Ex. 5 | Ex. 6 | Ex. 7 | Ex. 8 |
|---|---|---|---|---|---|---|
| Physical Tests |  |  |  |  |  |  |
| Model 1001 Adhesion (Belmar) | D 5178 (modified)* | Pass | Pass | Pass | Pass | Pass |
| Plasticizer Resistance (Hot) | D 2199 | No change | No change | No change | No change | No change |
| Plasticizer Resistance (Cold) | D 2199 | No change | No change | No change | No change | No change |
| Hot/Cold Check Test | D 1211 | Pass | Pass | Pass | Pass | Pass |
| Fade Resistance | G-53 | 8 | 8 | 8 | 8 | 8 |
| Dry Film Thickness | D 6132, on wood | 2.2 mils | 2.4 mils | 2.3 mils | 1.8 mils | 1.8 mils |
| Stain Resistance (Reagents) |  |  |  |  |  |  |
| 10% Citric Acid | D 1308, 3.1.1 | 10 | 10 | 10 | 10 | 10 |
| Water | D 1308, 3.1.1 | 10 | 10 | 10 | 10 | 10 |
| Mustard | D 1308, 3.1.1 | 10 | 10 | 10 | 10 | 10 |
| Iodine | D 1308, 3.1.1 | 10 | 10 | 10 | 10 | 10 |
| Ink | D 1308, 3.1.1 | 10 | 10 | 10 | 10 | 10 |
| Coffee | D 1308, 3.1.1 | 10 | 10 | 10 | 10 | 10 |
| Ammonia | D 1308, 3.1.1 | 8 | 10 | 10 | 10 | 10 |
| Rubbing Alcohol | D 1308, 3.1.1 | 6 | 10 | 10 | 10 | 10 |
| Vinegar | D 1308, 3.1.1 | 10 | 10 | 10 | 10 | 10 |
| Naptha | D 1308, 3.1.1 | 10 | 10 | 10 | 10 | 10 |
| Acetone | D 1308, 3.1.1 | 10 | 10 | 10 | 10 | 10 |
| Liquid Joy Detergent | D 1308, 3.1.1 | 10 | 10 | 10 | 10 | 10 |
| Fingernail polish | D 1308, 3.1.1 | 10 | 10 | 10 | 10 | 10 |
| Merthiolate | D 1308, 3.1.1 | 10 | 10 | 10 | 10 | 10 |

RATINGS:
1 = Fail,
10 = No effect
*Modification is the use of the Model 1001 Organic Coatings adhesion tester in place of the Belmar (Balanced Beam) tester.

Comparative Example 9 and Examples 10-13

In Comparative Example 9, a test panel was sprayed with REL-VETTE (available from Akzo Nobel Coatings Inc.). In Examples 10-13 the percentages of antimicrobial agent are given by weight of non-volatiles. Example 10 is a test panel sprayed with REL-VETTE formulated with 0.25% Ciba's IRGAGUARD B1000. Example 11 is a test panel sprayed with REL-VETTE formulated with 0.5% Ciba's IRGAGUARD B1000. Example 12 is a test panel sprayed with REL-VETTE formulated with 0.25% Clariant's PDQ. Example 13 is a test panel sprayed with REL-VETTE formulated with 0.5% Clariant's PDQ.

The coating properties of Comparative Example 9 and Examples 10-13 were tested and the results are shown in Table 3.

TABLE 3

|  | ASTM Reference | Comp. Ex. 9 | Ex. 10 | Ex. 11 | Ex. 12 | Ex. 13 |
|---|---|---|---|---|---|---|
| Physical Tests | | | | | | |
| Model 1001 Adhesion (Belmar) | D 5178 (modified)* | Pass | Pass | Pass | Pass | Pass |
| Plasticizer Resistance (Hot) | D 2199 | Faint imprint | Faint imprint | Faint imprint | Faint imprint | Faint imprint |
| Plasticizer Resistance (Cold) | D 2199 | No change | No change | No change | No change | No change |
| Hot/Cold Check Test | D 1211 | Pass | Pass | Pass | Pass | Pass |
| Fade Resistance | G-53 | 6 | 8 | 8 | 8 | 8 |
| Dry Film Thickness | D 6132, on wood | 1.8 mils | 1.5 mils | 1.3 mils | 1.2 mils | 1.5 mils |
| Stain Resistance (Reagents) | | | | | | |
| 10% Citric Acid | D 1308, 3.1.1 | 10 | 10 | 10 | 10 | 10 |
| Water | D 1308, 3.1.1 | 10 | 10 | 10 | 10 | 10 |
| Mustard | D 1308, 3.1.1 | 10 | 10 | 10 | 10 | 10 |
| Iodine | D 1308, 3.1.1 | 10 | 10 | 10 | 10 | 10 |
| Ink | D 1308, 3.1.1 | 10 | 8 | 10 | 10 | 8 |
| Coffee | D 1308, 3.1.1 | 10 | 10 | 10 | 10 | 10 |
| Ammonia | D 1308, 3.1.1 | 10 | 6 | 8 | 6 | 10 |
| Rubbing Alcohol | D 1308, 3.1.1 | 8 | 10 | 8 | 10 | 8 |
| Vinegar | D 1308, 3.1.1 | 10 | 10 | 10 | 10 | 10 |
| Naptha | D 1308, 3.1.1 | 10 | 10 | 10 | 10 | 10 |
| Acetone | D 1308, 3.1.1 | 6 | 4 | 6 | 6 | 6 |
| Liquid Joy Detergent | D 1308, 3.1.1 | 10 | 10 | 10 | 10 | 10 |
| Fingernail polish | D 1308, 3.1.1 | 10 | 10 | 10 | 10 | 10 |
| Merthiolate | D 1308, 3.1.1 | 10 | 10 | 10 | 10 | 10 |

RATINGS:
1 = Fail,
10 = No effect
*Modification is the use of the Model 1001 Organic Coatings adhesion tester in place of the Belmar (Balanced Beam) tester.

Bacterial growth inhibition testing was conducted for Comparative Examples 4 and 9, and Examples 5, 6, 10 and 11. Panels of each of these Examples and Comparative Examples were placed on the top layer of the agar containing bacteria from diluted overnight cultures. The antimicrobial activity as expressed by zone of inhibition (ZI) and Vinson Rating (VR) was then examined after incubation at 37° for 24 h. In each case, the agar was a casein-soymeal peptone agar (CASO e.g. from Merk Darmstad, Germany) for the bottom and top layer. The bacterial suspension in each case was diluted in 0.85% NaCl solution pH 7.2+/−0.2.

The results of the bacterial growth inhibition testing are shown in Table 4. FIGS. 1-12 also show the results of bacterial growth inhibition testing, but the panels used for Comparative Examples 4 and 9 indicate a zone of inhibition due to the panels of the examples and comparative examples being stored with their coatings face-to-face prior to testing.

TABLE 4

| | Staphylococcus aureus ATCC 9144 | | Escherichia coli NCTC 8196 | |
|---|---|---|---|---|
| Samples: Wood | ZI | VR | ZI | VR |
| Comp. Ex. 4 | 0/0 | 0/0 | 0/0 | 0/0 |
| Ex. 5 | 9/10 | 4/4 | 3/4 | 4/4 |
| Ex. 6 | 12/14 | 4/4 | 6/6 | 4/4 |
| Comp. Ex. 9 | 0/0 | 0/0 | 0/0 | 0/0 |

TABLE 4-continued

| | Staphylococcus aureus ATCC 9144 | | Escherichia coli NCTC 8196 | |
|---|---|---|---|---|
| Samples: Wood | ZI | VR | ZI | VR |
| Ex. 10 | 12/13 | 4/4 | 6/7 | 4/4 |
| Ex. 11 | 18/20 | 4/4 | 10/12 | 4/4 |

All tests were performed twice and both results are given in the table
Legend:
ZI = zone of inhibition in mm
VR = Vinson Rating, for growth under the disc
4 = no growth (good activity),
2 = isolated colonies (moderate activity),
0 = strong growth (no activity) (L. J. Vinson et al. J. Pharm. Sci. 50, 827-830, 1961)

The results demonstrate the effectiveness of the inventive acid-catalyzed coating composition formulated with an antimicrobial agent. Comparative Examples 4 and 9, without the antimicrobial agent, have no zone of inhibition (ZI) surrounding the sample, and no inhibition of growth under the sample, as shown by the Vinson Rating (VR). Examples 5, 6, 10 and 11 have significant and visible zones of inhibition (ZI) and good activity under the sample (VR). There are also significant differences when comparing the antimicrobial formulations of REL-VIRON to those of REL-VETTE. These acid catalyzed coating compositions differ in that REL-VETTE includes a plasticizer and will have nitrocellulose in about 20—about 30% by weight non-volatiles. There usually is no plasticizer in REL-VIRON and only about 1—about 10% by weight non-volatiles of nitrocellulose.

The invention claimed is:

1. A coating composition comprising an acid-catalyzed coating composition comprising one or more aminoplast resins, one or more backbone resins which contain functional groups that will react with the aminoplast resin or resins, at least one acid catalyst, and an antimicrobial agent comprising 2,4,4-trichloro-2-hydroxydiphenyl ether, or N-(trichloromethylthio)phthalimide, wherein said antimicrobial agent comprises from about 0.1% to about 0.5% by weight of non-volatiles.

2. The coating composition of claim 1, wherein the coating composition comprises:
about 40-about 60% by weight of non-volatiles of the one or more backbone resins; about 20-about 40% by weight of non-volatiles of at least one crosslinker; about 60-about 70% by weight of volatiles of at least one carrier; and about 2-about 4% by weight of non-volatiles of the at least one acid catalyst.

3. An article coated with the antimicrobial acid-catalyzed coating composition of claim 1.

* * * * *